United States Patent [19]

Scholten et al.

[11] Patent Number: 4,969,888

[45] Date of Patent: Nov. 13, 1990

[54] SURGICAL PROTOCOL FOR FIXATION OF OSTEOPOROTIC BONE USING INFLATABLE DEVICE

[76] Inventors: Arie Scholten, 4175 Tamayo St., Fremont, Calif. 94536; Mark A. Reiley, 333 63rd St., Oakland, Calif. 94618

[21] Appl. No.: 308,724

[22] Filed: Feb. 9, 1989

[51] Int. Cl.⁵ ............................................. A61B 17/56
[52] U.S. Cl. ....................................... 606/94; 606/60; 606/95
[58] Field of Search .................... 128/92 VP, 92 VQ; 606/94, 95, 60

[56] References Cited

U.S. PATENT DOCUMENTS

| | | | |
|---|---|---|---|
| 3,091,237 | 5/1963 | Skinner | 128/60 |
| 3,112,743 | 12/1963 | Cochran et al. | 128/92 VP |
| 3,648,294 | 3/1972 | Shahrestani | 128/92 |
| 3,875,595 | 4/1975 | Froning | 128/92 |
| 3,889,665 | 6/1975 | Ling et al. | 128/92 VP X |
| 4,274,163 | 6/1981 | Malcom et al. | 128/92 |
| 4,462,394 | 7/1984 | Jacobs | 128/92 VP |
| 4,466,435 | 8/1984 | Murray | 128/303 |
| 4,488,549 | 12/1984 | Lee et al. | 128/303 |
| 4,562,598 | 1/1986 | Kranz | 128/92 |
| 4,625,722 | 12/1986 | Murray | 128/92 |
| 4,627,434 | 12/1986 | Murray | 128/92 VP |
| 4,627,434 | 12/1986 | Murray | 128/303 |
| 4,628,945 | 12/1986 | Johnson, Jr. | 128/80 |
| 4,714,478 | 12/1987 | Fischer | 623/23 |
| 4,772,287 | 9/1988 | Ray et al. | 623/17 |

OTHER PUBLICATIONS

Howmedica Exeter Pressurizer 1979, 2 pages.
Journal of B & J Surgery, pp. 1665-1676, vol. 54A #8, 12/1972.

Primary Examiner—Robert A. Hafer
Assistant Examiner—Kevin G. Rooney
Attorney, Agent, or Firm—Townsend and Townsend

[57] ABSTRACT

A method and apparatus for the fixation of osteoporotic bones and especially vertebral body compression fractures, Colles' fractures and fractures of the proximal humerus. The method of the present invention includes a series of steps including penetrating the bone having the fracture with a guide pin, drilling the osteoporotic bone marrow of the bone to enlarge the cavity to be treated, following which a bone specific inflatable device is inserted in the cavity and inflated. The expansion of the device causes a compacting of the osteoporotic bone marrow against the inner surface of the outer wall of the bone to be treated to further enlarge the cavity. When this occurs, a flowable synthetic bone material or methyl methacrylate cement is directed into the cavity and allowed to set to a hardened condition. Following this, the instruments are removed. In the fixation of vertebral body fractures, an elliptical inflatable device is first used to initiate the compacting of the osteoporotic bone marrow, following which a checker-shaped inflatable device is inserted into the cavity to further compact the osteoporotic bone marrow in all directions. In the fixation of Colles' fractures and proximal humerus fractures, a gourd-shaped inflatable device is used to compact the osteoporotic bone marrow.

28 Claims, 11 Drawing Sheets

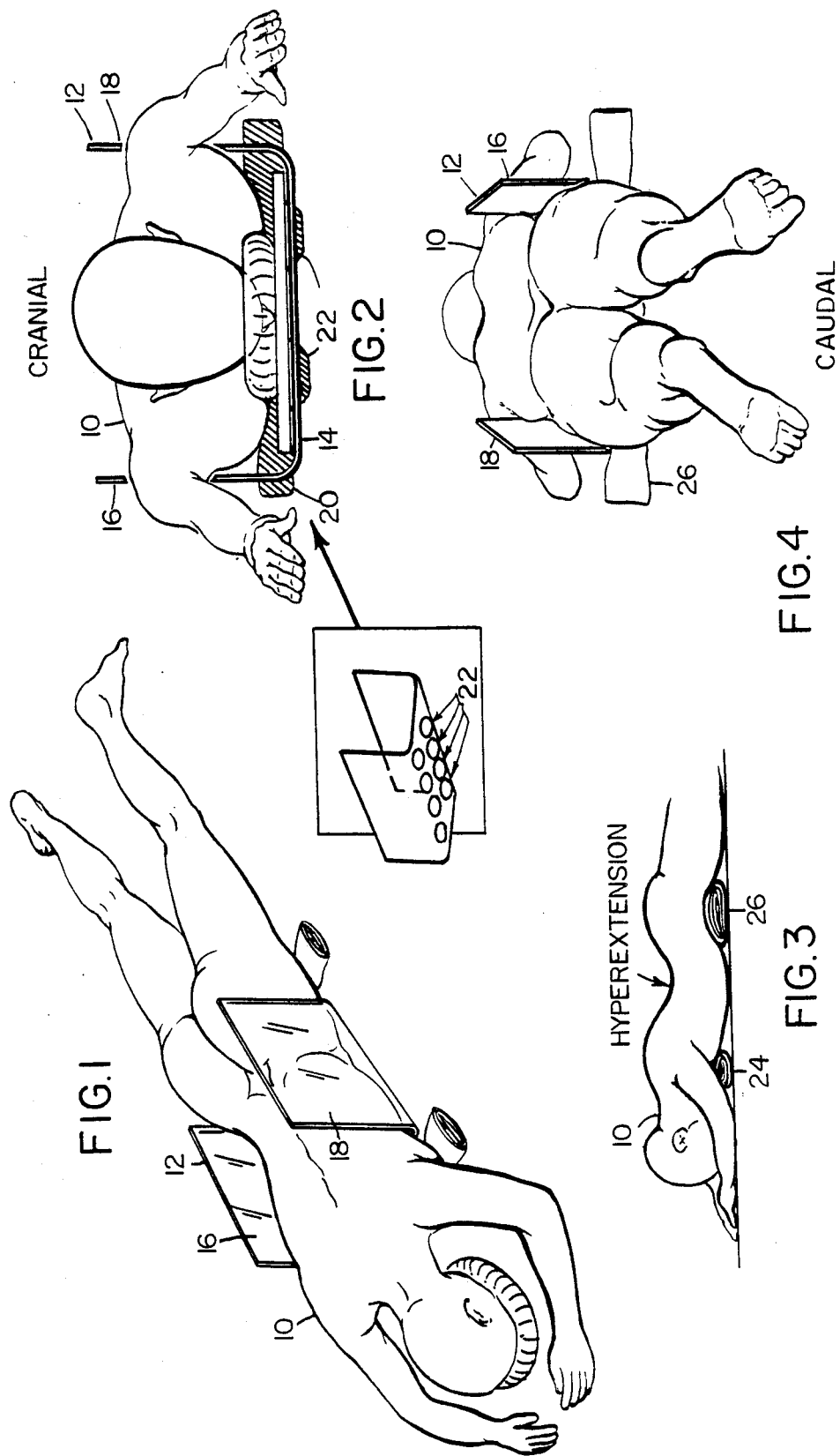

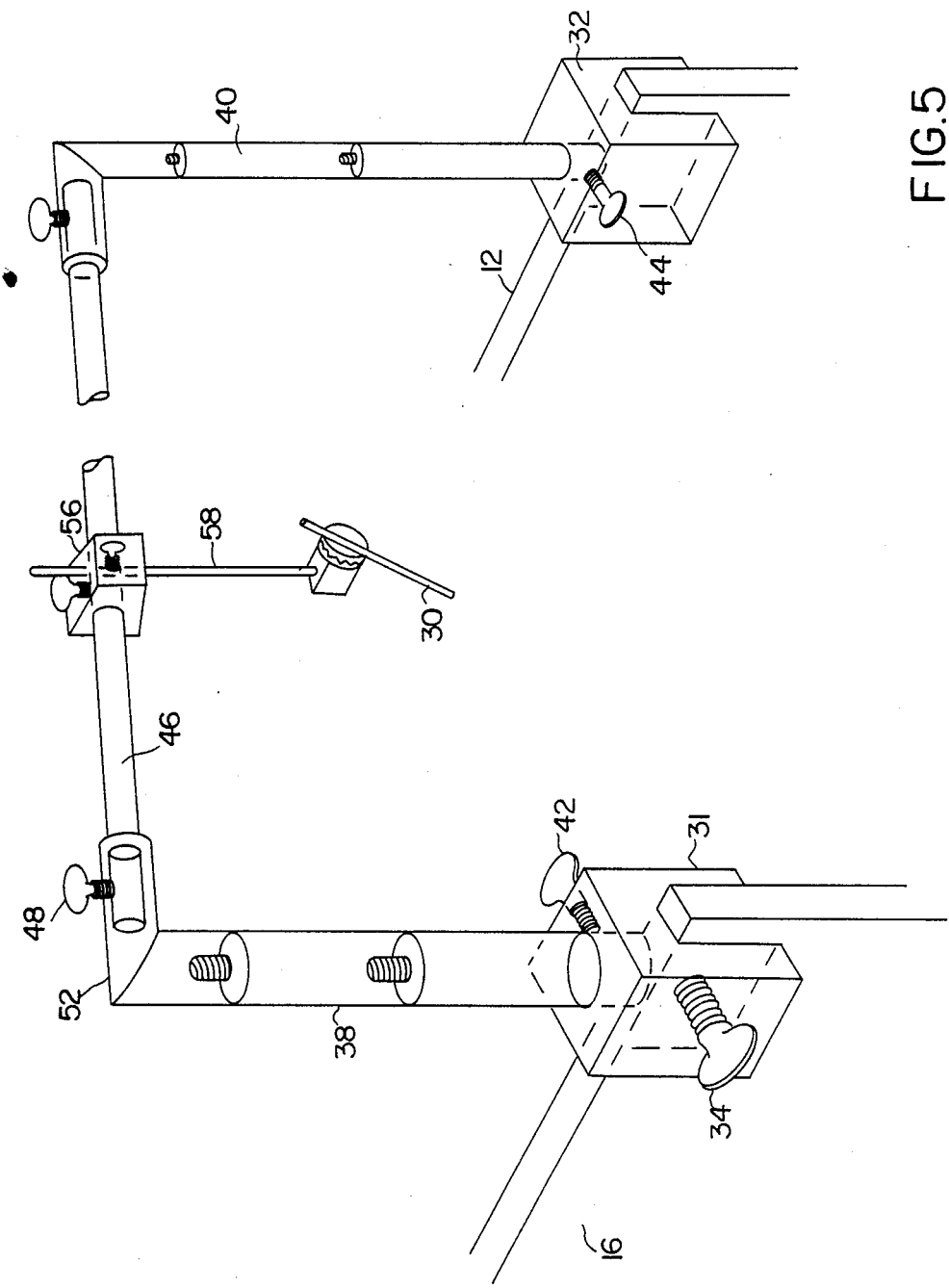

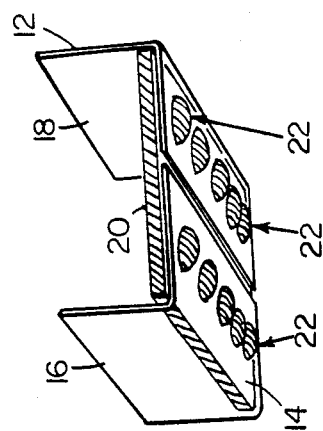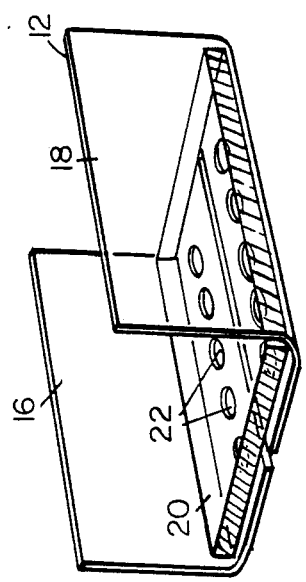

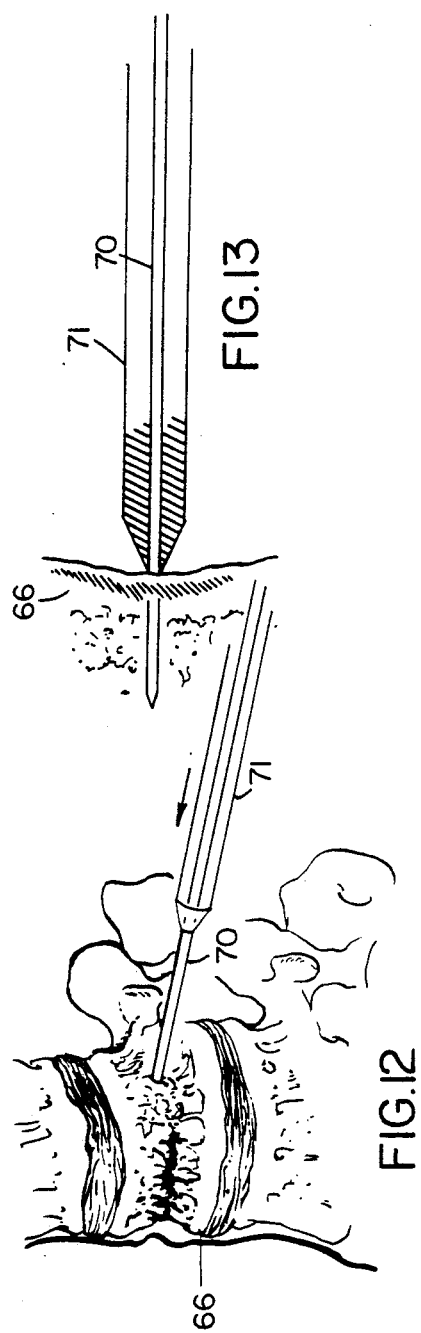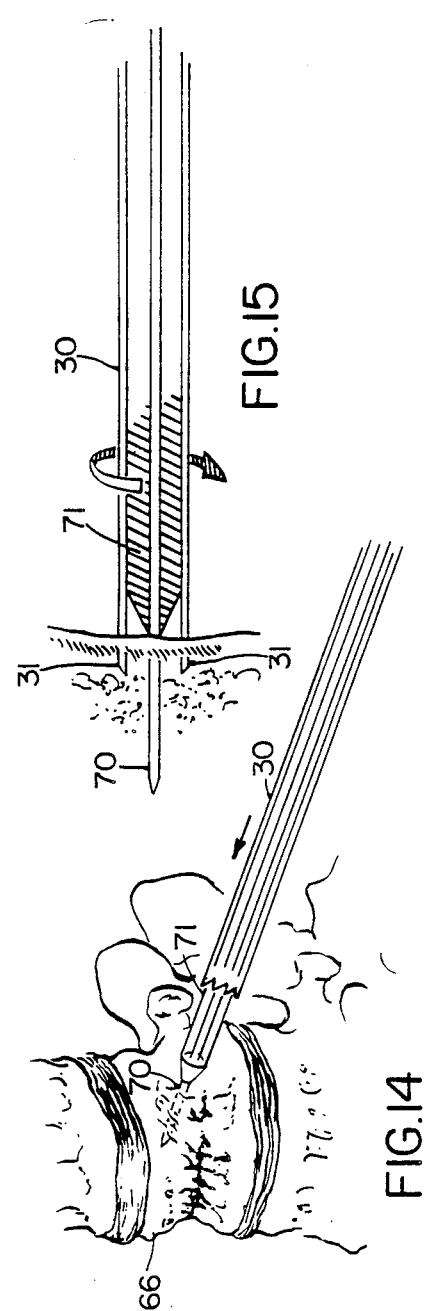

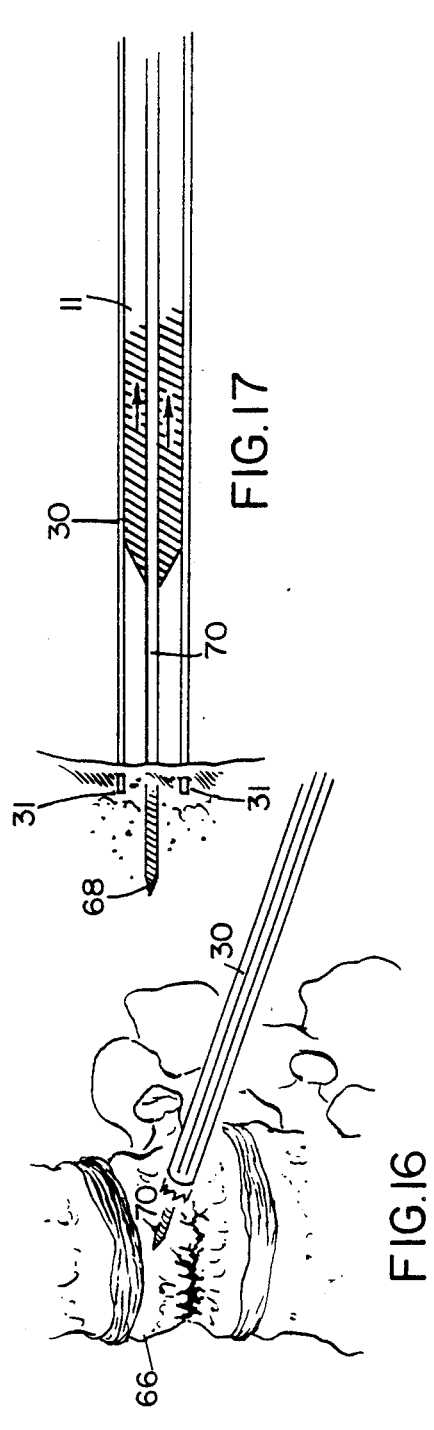
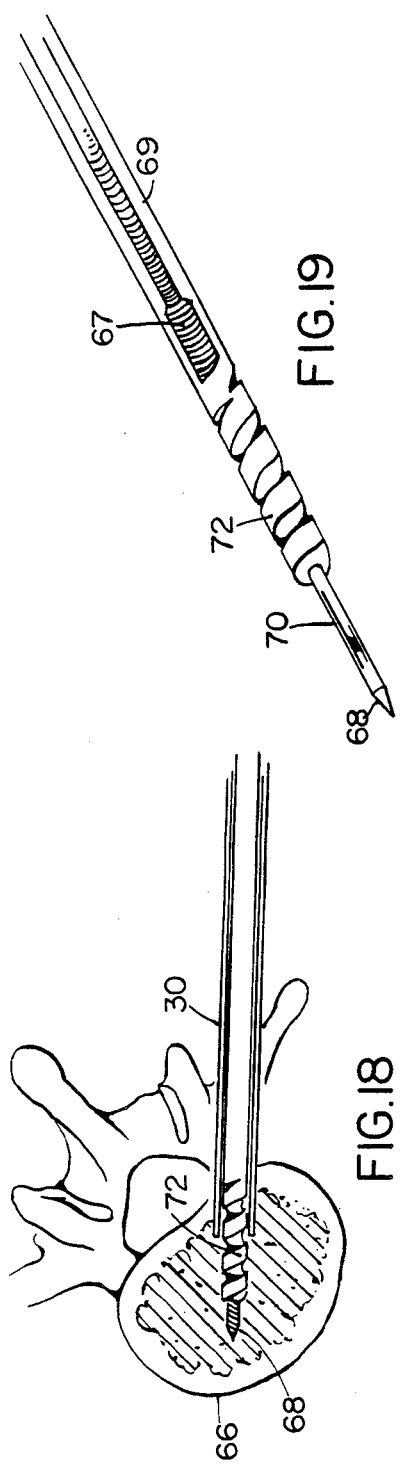
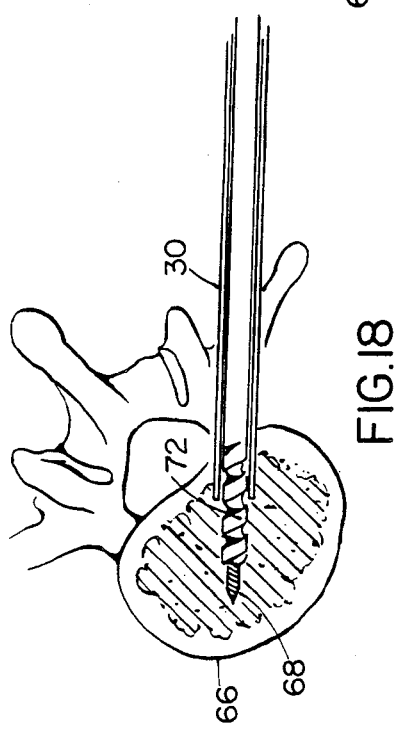

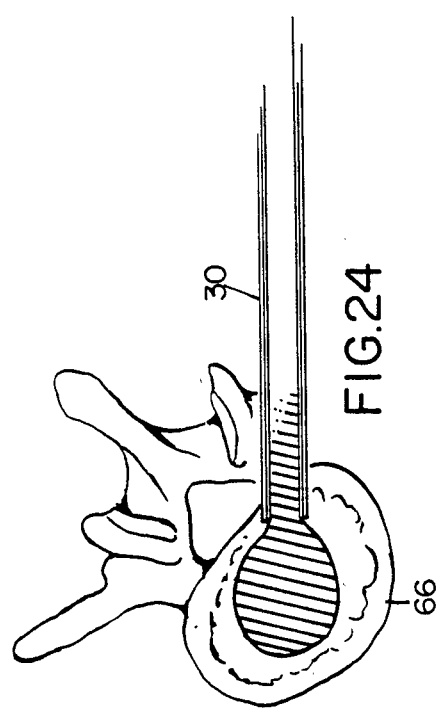
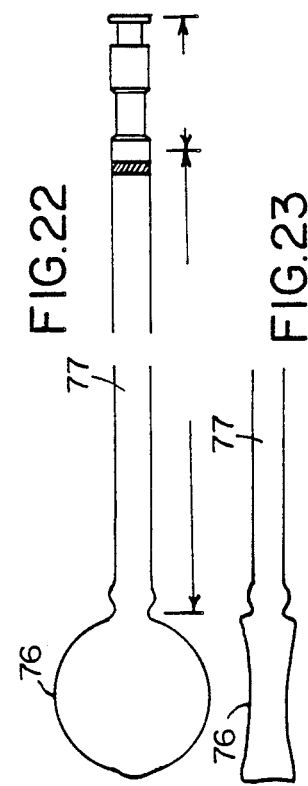
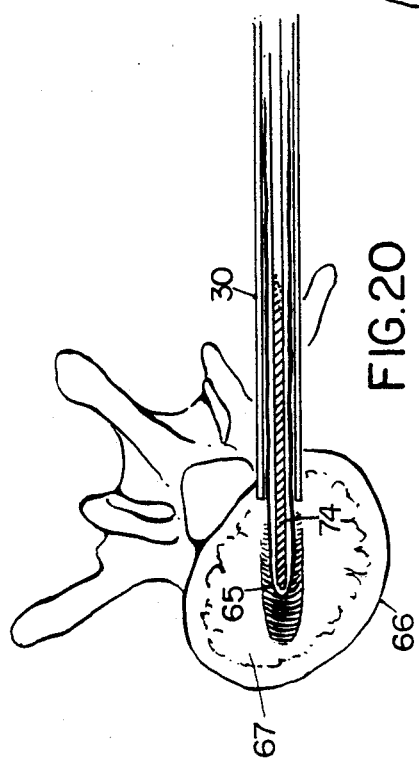
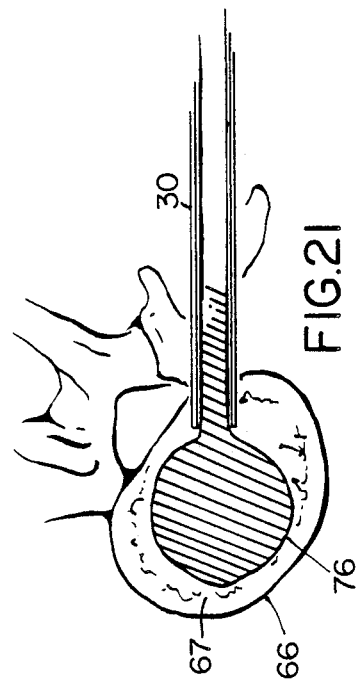

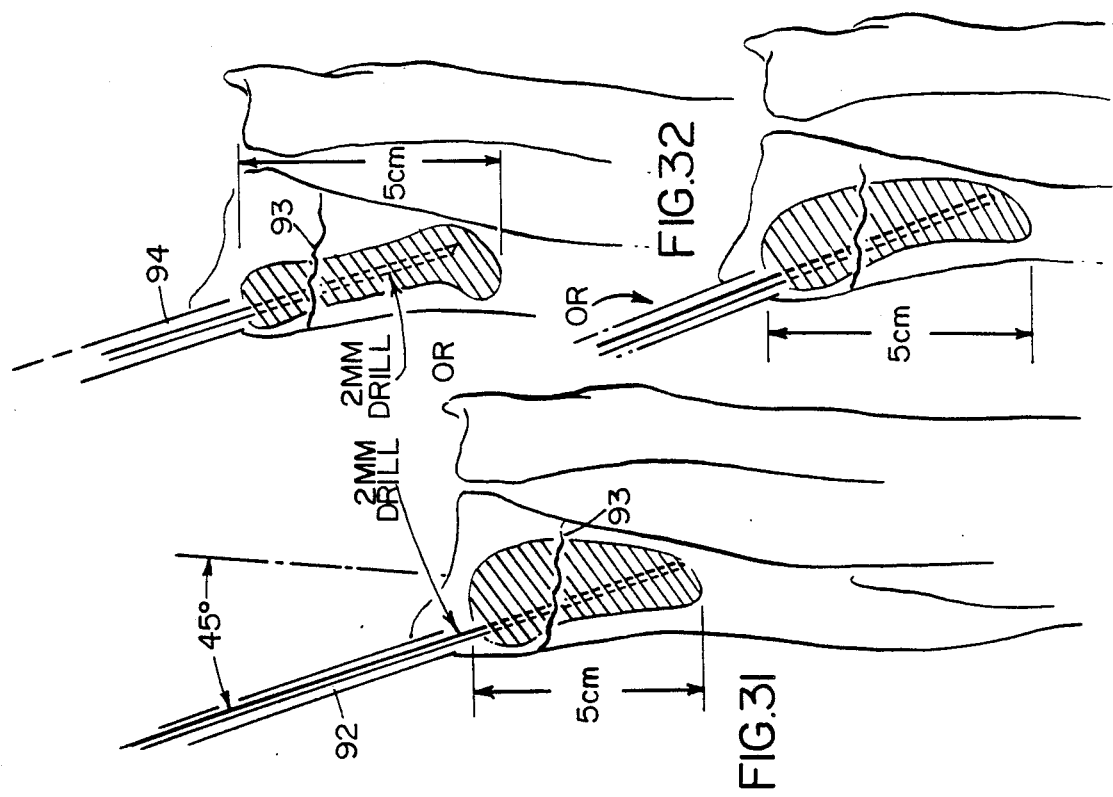
FIG.32
FIG.31
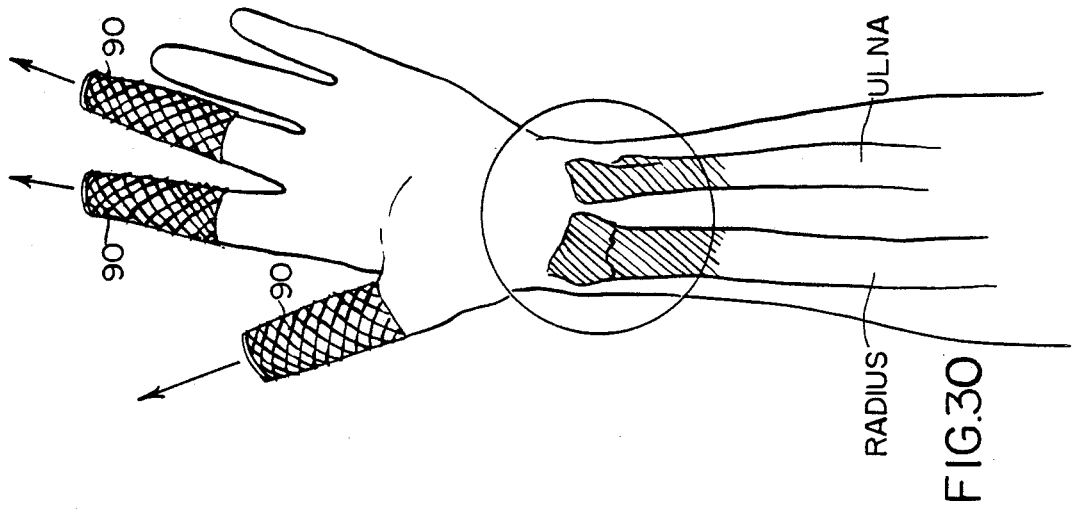
FIG.30
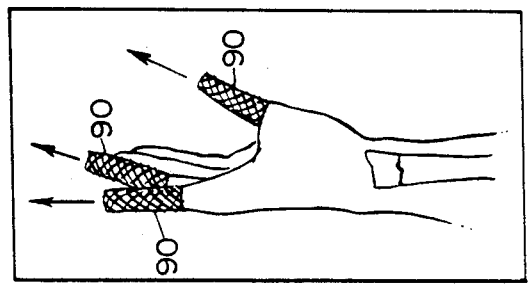
FIG.29

SURGICAL PROTOCOL FOR FIXATION OF OSTEOPOROTIC BONE USING INFLATABLE DEVICE

This invention relates to improvements in the surgical treatment of bone conditions of the human and other animal body systems due to osteoporosis and, more particularly, to a method and apparatus for use in correcting such conditions.

BACKGROUND OF THE INVENTION

Every year in the United States there occurs approximately 1.2 million fractures due to osteoporosis. Nine hundred thousand (900,000) of those fractures occur in bones which can be treated with the percutaneous balloon technology of the present invention which includes instant fixation by methyl methacrylate cement or with liquid artificial bone substitutes. Those fractures which can be treated by the method and apparatus of the present invention are the Colles' fracture, the proximal humerus fracture, and the vertebral body compressions fracture.

Osteoporotic vertebral body compression fractures are currently treated with bed rest, analgesics, and intravenous hydration during the first week after onset of the problem. These steps are followed by the prescription of a soft or firm spinal corset, depending upon the physician's preference. In most cases, the corset is not worn because the patient suffers much discomfort and oftentimes greater discomfort than that due to the fracture of the vertebral body. The fracture pain lasts from two to eight months. In many cases, patients with osteoporotic vertebral body collapse fractures require about one week in an acute care hospital and two to three weeks in an extended care facility until they are able to move about independently and with only moderate pain. Current treatment does not substantially alter the conditions of the vertebral body.

The current management of osteoporotic shoulder fractures includes either long term immobilization in a sling, followed by lengthy physical therapy. If the fracture is in three or four parts, the fracture is treated with a shoulder hemiarthroplasty. Long term stiffness is the rule, following either treatment due to long term immobilization and/or extensive wound healing.

Osteoporotic Colles' fractures of the wrist in the elderly are currently treated in three different ways: (1) they are treated with closed reduction and application of a short arm cast for one or more weeks; (2) they can be treated with a short arm cast without reduction; and (3) they may be treated with closed reduction and pins and plaster immobilization for eight weeks. All treatment modalities result in considerable stiffness and have frequent malunions of the fractures.

Because of the problems associated with the treatment of vertebral body fractures, Colles' fractures, shoulder fractures and other osteoporotic conditions similar thereto, a need has existed for a method and apparatus to improve on the protocol for treating such fractures such as shortening the time in which a patient suffers pain due to such fracture. The present invention provides apparatus and a method of percutaneous fracture fixation which satisfies this need.

SUMMARY OF THE INVENTION

This invention relates to a method and apparatus for the fixation of fractures of osteoporotic bones. The invention is especially suitable for use in the fixation of vertebral body compression fractures, Colles' fractures and fractures of the proximal humerus. The method of the present invention includes a series of steps including forming an incision in the body and penetrating the bone having the fracture with instruments including a guide pin and a cannula, drilling the osteoporotic bone marrow of the bone to enlarge the cavity or passage to be treated, following which an inflatable device, such as an expandable balloon, is inserted in the cavity and inflated. The expansion of the balloon causes a compacting of the osteoporotic bone marrow against the inner surface of the outer cortical wall of the bone to be treated to further enlarge the cavity. Then, a flowable synthetic bone material or methyl methacrylate cement is directed into the cavity and allowed to set to a hardened condition. Following this, the instruments are removed and the incision in the skin is covered with a bandage.

In the fixation of vertebral body fractures, an elliptical inflatable device is first used, if needed, to initiate the compacting of the osteoporotic bone marrow and to commence the formation of a cavity or passage in the osteoporotic bone marrow, following which a checker-shaped inflatable device is inserted into the cavity to further compact the osteoporotic bone marrow in all directions. In the fixation of Colles' fractures and proximal humerus fractures, a gourd-shaped inflatable device is used to compact the osteoporotic bone marrow.

It is the intention of the present invention to provide, in each case of a fracture of osteoporotic bone, an inflatable device that has a shape preferably approximating the internal surface configuration of the cortical bone in which the device is used. Thus, the inner surface configuration of the cortical bone of a vertebral body is disk-shaped or checker-shaped, the cortical bone of distal radius is gourd-shaped and the cortical bone of the proximal humerus is also gourd-shaped.

BRIEF DESCRIPTION OF THE DRAWINGS

FIG. 1 is a perspective view of a patient about to undergo the surgical treatment of vertebral body fixation in accordance with the method of the present invention, the patient lying prone on a U-shaped holder;

FIG. 2 is a front elevational view of the patient on the holder;

FIG. 3 is a side elevational view of the patient, showing hyperextension of the spine of the patient;

FIG. 4 is a perspective view of the rear portion of the patient showing the patient lying between the sides of the holder;

FIG. 5 is a stabilizer bracket for a guide pin and a cannula forming parts of the apparatus for carrying out the method of the present invention;

FIG. 6 is a perspective view of the patient holder shown in FIGS. 1, 2 and 4;

FIG. 7 is another perspective view of the holder of FIG. 6 looking upwardly from the bottom thereof;

FIG. 12 is a perspective view of the guide pin placed within the vertebral body and a tissue expander sliding on the guide pin to the vertebral body;

FIG. 13 is a side elevational view of the tissue expander over the guide pin;

FIG. 14 is a view similar to FIG. 12 but showing a cannula carried by the tissue expander toward the vertebral body;

FIG. 15 is a view similar to FIG. 13 but showing teeth of the cannula embedded in the outer wall of the vertebral body;

FIG. 16 is a view similar to FIG. 14 but showing another view of the cannula embedded in the cortical wall of the vertebral body;

FIG. 17 is a view similar to FIG. 15 but showing the withdrawal of the tissue expander through the cannula;

FIG. 18 is a view similar to FIG. 11 but showing a drill guided into the vertebral body by the guide pin through the cannula;

FIG. 19 is an enlarged perspective view of the drill of FIG. 18;

FIG. 20 is a view similar to FIG. 18 but showing an elliptical inflatable device inserted into the vertebral body to expand the osteoporotic bone marrow in the vertebral body;

FIG. 21 is a checker-shaped inflatable device in the vertebral body to complete the expansion of the osteoporotic bone marrow in the vertebral body;

FIG. 22 is a top plan view of the checker-shaped inflatable device of FIG. 21;

FIG. 23 is a side elevational view of the checker-shaped inflatable device of FIG. 22;

FIG. 24 is a view similar to FIGS. 20 and 21 but showing the insertion of the inflatable device of FIG. 22 into a vertebral body;

FIG. 29 is a schematic top plan view of a distal radius fracture of the wrist, the fracture at the end of the radius being aligned with Chinese finger traps;

FIG. 30 is a view similar to FIG. 29 but looking in a different direction at the hand but illustrating the fracture;

FIG. 31 is a view of the fracture with the guide pin being inserted through the interface of the fracture;

FIG. 32 is a view similar to FIG. 31 but showing a drill in the radius, and the area to be filled with liquid bone or methyl methacrylate cement;

DETAILED DESCRIPTION OF THE DRAWINGS

Figure 8:
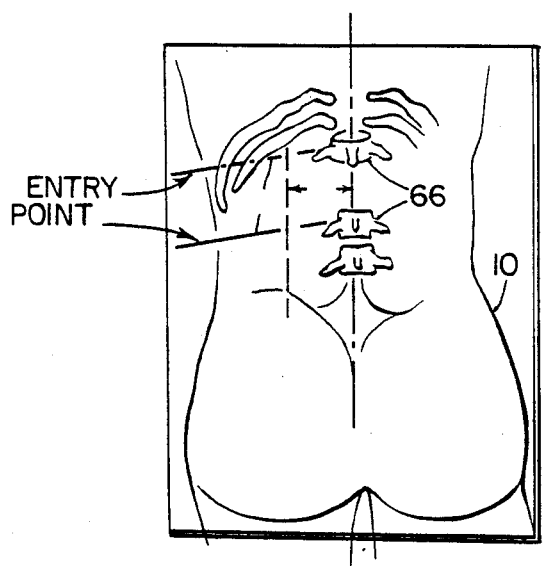
FIG. 8 is a top plan view of the portion of the patient showing several vertebral bodies of the patient and the way in which the a guide pin enters a patient for carrying out the method of the present invention.

Percutaneous vertebral body fixation is indicated for all causes of spontaneous osteoporotic vertebral body collapse fractures except those due to infection or neoplasia. The etiology of the osteoporosis should be diagnosed prior to fixation. Concomitant endocrine therapy, chemotherapy or radiation is not contraindicated with percutaneous vertebral fracture fixation.

Impending vertebral body collapse due to osteoporosis as determined by the presence of previous collapse fractures and increased uptake on technetium-99 bone scan in a non-collapsed vertebral body. Various CT density values may eventually correlate with impending vertebral body collapse and be utilized to predict impending vertebral body fractures.

Contradictions of such fixation are as follows:
Presence of pyogenic infection;
Presence of tuberculous infection;
Presence of neoplasia;
Presence of sepsis;
High velocity spinal fractures;
Fractures above the level of T-6; and
Fractures which demonstrated widened pedicles on AP spine x-rays.

In carrying out the teachings of the method of the present invention as to osteoporotic vertebral fixation, a patient 10 is placed on a generally U-shaped holder 12 so that the patient lies above the central part 14 of holder 12 and between a pair of spaced sides 16 and 18 as shown in FIGS. 1, 2 and 4. Holder 12 can be of any suitable construction, such as metal or plastic and is constructed to render the patient generally immovable when the patient is prone as shown in FIGS. 1-4. The length of sides 16 and 18 is preferably sufficient to achieve the aim of rendering the patient generally immovable.

Typically, the length of sides 16 and 18 is approximately 12 to 15 inches. For the comfort of the patient, a cushion 20 is provided above central part 14 as shown in FIG. 2. The central part 14 has holes 22 therethrough (FIGS. 6 and 7) and the holes are for the purpose of receiving circular portions of the cushion 20 formed due to the weight of the patients to anchor the cushion in place and to prevent it from moving relative to holder 12 when the patient's body is on the cushion as shown in FIG. 2. This assures that the cushion will not contribute to the movement of the patient relative to the holder. Pads 24 and 26 are placed at the chest and hip regions of the patient for the comfort of the patient and to extend the spine.

FIG. 5 shows a support bracket 28 adjustably mounted on the sides 16 and 18 of holder 12. The purpose of bracket 28 is to support a cannula 30 and guide pin 70 forming part of the apparatus of the present invention. Cannula 30 will be described hereinafter in more detail.

Bracket 28 includes a pair of clamps 31 and 32 for releasably connecting the bracket to respective sides 16 and 18 of holder 12 by means of thumb screws 34. Bracket 28 further includes a pair of legs 38 and 40 which are made up of connectable extensions as shown in FIG. 5. Legs 38 and 40 are releasably connected to respective clamps 31 and 32 by thumb screws 42 and 44. A rod 46 is connected by thumb screws 48 and 50 to end sleeves 52 and 54 on the upper ends of respective legs 38 and 40. Rod 46 can be rotated in the sleeves 52 and 54 to thereby rotate a clamp 56 coupled to the rod 46 and having a leg 58 on which cannula 30 and guide pin 70 are adjustably mounted. Thus, the cannula can be moved toward or away from legs 38 and 40 and can rotate about the longitudinal axis of rod 46. In this way, the cannula can be adjusted as to the distance from the patient to rod 46 as well adjust the position of the bracket 28 by means of shifting clamps 31 and 32 along the sides of holder 12.

The teachings of the method of the present invention will be hereinafter described with respect to treatment of a person with osteoporotic spine disease. The presence of such disease is evidenced by a plain film spinal x-rays and either CAT-scan evidence of impending fracture or plain film x-ray evidence of vertebral body collapse. In obtaining such evidence, both sagittal and coronal CAT-scans should be obtained before the performance of the method of the present invention. The coronal scan is also needed to determine the width of the vertebral body which is to be treated and also to rule out the presence of posterior displacement of the colon which can interfere with the posterolateral approach which generally occurs in four percent of the patients. If the colon is noted, the approach must be altered to the other side of the body.

The sagittal CAT-scan is needed to determine the height of the vertebral body to be treated. If an acute compression fracture is present, then the appropriate height is determined by the height of the vertebral body located superior to the fracture. If the patient has an acute fracture of a vertebral body, the patient is to be placed prone in the manner shown in FIGS. 1–4.

Attempts to reconstitute the height of the vertebral body should be made by hyperextending the patient's spine as shown in FIG. 3. If the patient has an impending fracture of a vertebral body, then the patient can be positioned either prone as shown in FIGS. 1–4 or on his side depending upon the surgeon's preference. If on the side, the patient is rendered immovable by suitable structure for holding the patient in one position during the time that the method of the present invention is being performed.

The posterolateral approach is used whether the patient is prone (FIGS. 1–4) or in the lateral position. Then the entry point on the skin is determined radiologically and is located approximately 10 cm from the midline and just inferior to a rib if present at that level as shown in FIG. 8.

Figure 9:
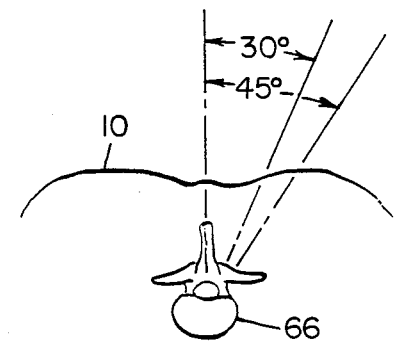
FIG. 9 is a schematic front elevational view of the patient and a vertebral body of the patient showing the entry angles of the guide pin of the apparatus of the present invention.

FIG. 8 shows the entry points of the instruments for carrying out the method of the present invention for two vertebral bodies spaced from each other. The instrument shown in FIG. 8 is a guide pin 70 which enters the patient at an inoision 62 (FIG. 8). A choice of angle of entry of the guide pin 70 can be 30° to 45° as shown in FIG. 9. The vertebral body to be injected is located fluoroscopically. The skin, underlying soft tissue and lateral cortex of the vertebral body are injected with a long spinal needle. General anesthesia is not advisable.

The surgical procedure for treating a vertebral body is as follows:

The vertebral body 66 to be treated (FIGS. 10 and 11) is penetrated by the pointed end 68 of guide pin 70 which enters the vertebral body between the inferior and superior end plates of the body 66 and into the posterior quarter of the vertebral body. Pedicles are to be ignored. The guide pin penetrates to a depth in the range of 60 to 80% across vertebral body 66 as shown in FIG. 11. Placement of the pin is fluoroscopically monitored. Any further penetration beyond 70% runs the risk of perforation of the vertebral body and an adjacent major vessel or lung.

Figure 10:
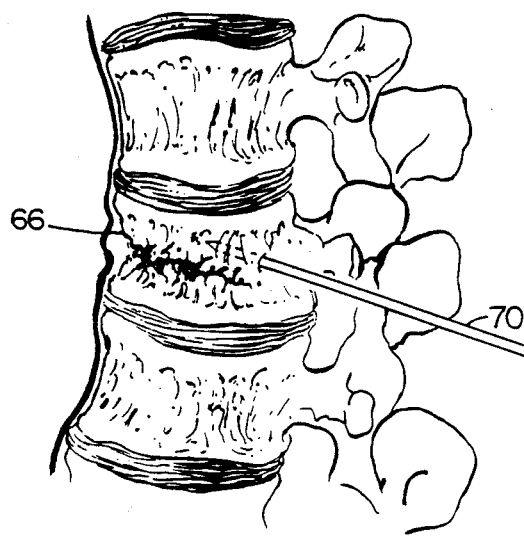
FIG. 10 is a side elevational view of the vertebrae, showing a guide pin inserted into one of the vertebral bodies.
Figure 11:
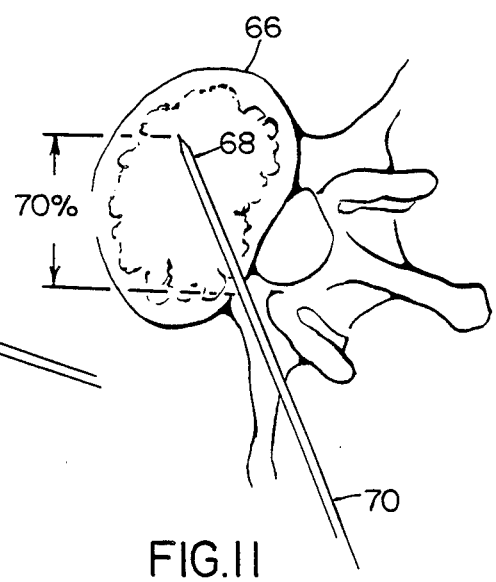
FIG. 11 is a top plan view of the guide pin inserted into the vertebral body.

With the guide pin penetrating the vertebral body 66 as shown in FIGS. 10 and 11, a soft tissue expander 71, which is a tubular member as shown in FIGS. 12 and 13, is inserted over the guide pin until the end of the expander makes contact with the vertebral body as shown in FIG. 13. Expander 71 then forms a guide for cannula 30 to guide the cannula toward the vertebral body to be treated.

When the cannula makes contact with the wall of the vertebral body, the cannula is rotated clockwise under pressure to force the teeth 31 of the cannula into the wall of the vertebral body 66 as shown in FIG. 15. This locks the cannula into the wall as shown in FIG. 16 so that the cannula can be coupled to bracket 28 (FIG. 5) for stabilization thereby. Then, the expander 71 can be removed from the interior of cannula 30 as shown in FIG. 17.

Once the cannula is stabilized, a drill stop is formed to prevent penetration of the far cortex of the vertebral body by drill 72 (FIGS. 18 and 19). The drill stop is formed by a shoulder 67 on pin 70 (FIG. 19) which is engageable with shoulder 69 on drill 72 and holding pin 70 with bracket 28.

Vertebral body 66 is drilled by a 4 mm drill 72. The drilling depth is monitored by fluoroscopy to the end of the guide 10. The drill is tubular and is guided by the guide pin 70 as shown in FIG. 19.

The next step to be performed in carrying out the method of the present invention is to withdraw the pointed guide pin 70 and replace it with a deflated elliptical device or chambered bladder or balloon 65. The elliptical balloon 65 is monitored fluoroscopically. This is achieved by inflating the elliptical balloon 65 to a pressure in the range of 50 to 300 psi with a radioopaque contrast medium by an injector as shown in FIG. 24. The purpose of the elliptical balloon 65 is to center a second, checker-shaped inflatable device or balloon 76 (FIGS. 21–23) in the interior of vertebral body 66. After the elliptical balloon is deflated and removed, checker-shaped or cylindrically shaped device of balloon 76 is inserted into the cannula and directed into the interior of vertebral body 66 as shown in FIG. 21.

The diameter of balloon 76 is determined by the preoperative CAT-scan results. The diameter is in the range of 1.0 cm to 3.5 cm. The axial height of the balloon (FIG. 23) is determined by the intra-operative reduction height of the vertebral body fracture. The height is in the range of 0.5 cm to 4.0 cm. If the balloon placement is somewhat eccentric, a smaller balloon may be needed. The balloon 76 has a neck 77, and the outer configuration of the balloon 76 is substantially the same as that of the inner surface of the cortical wall of the vertebral body 66.

The progress of balloon inflation is monitored fluoroscopically to ensure proper insertion of the balloon 76. The balloon is injected, gradually, with contrast as in the case of the elliptical balloon to a maximum height. This may require pressure as great as 300 psi to accomplish. The balloon's inflation should be monitored on the lateral fluoroscopic view of the spine. Posterior displacement of the bone into the spinal canal or full expansion of balloon 76 signals the termination of the chamber preparation. Further expansion of the balloon at this point could result in spinal cord or root injury.

As balloon 76 is inflated, it forces the osteoporotic bone marrow 67 laterally and outwardly of the wall of the vertebral body 66. This compacts the bone marrow and leaves a void in the interior of the vertebral body to be treated. The compacted bone marrow forms a dam to block any fracture of the vertebral body. Thus, when liquid synthetic bone or methyl methacrylate cement is forced into the void, the compacted bone marrow will substantially prevent flow through the fracture.

After the balloon 76 has been deflated it is removed from the cannula 30. An irrigation nozzle (not shown) is then inserted into the vertebral body 66. Irrigation is performed with normal saline solution. Irrigation should be performed until the effluent is reasonably clear.

Figure 26:
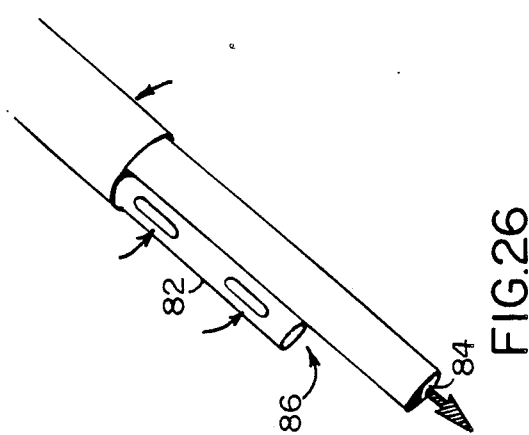
FIG. 26 is an enlarged, fragmentary perspective view for directing liquid bone or methyl methacrylate cement into the vertebral body.
Figure 25:
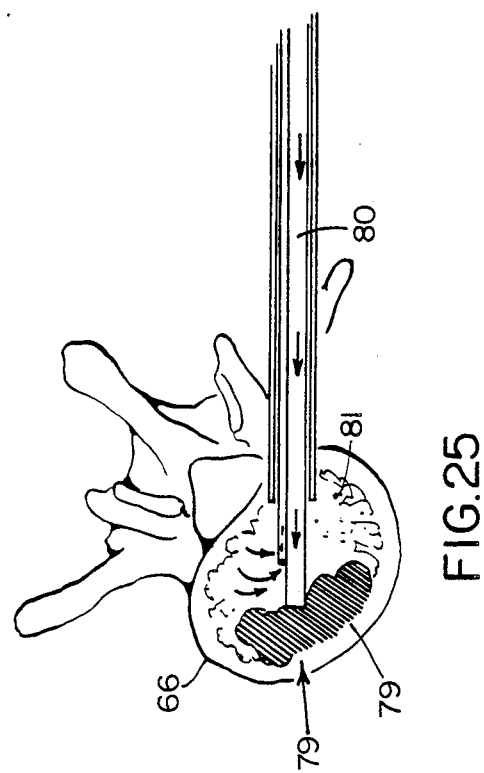
FIG. 25 is a view similar to FIG. 24 but showing the insertion of a liquid artificial bone or methyl methacrylate cement into the vertebral body to replace the osteoporotic bone marrow.

After the vertebral body has been irrigated, the artificial bone substitute, which may include a synthetic bone or methyl methacrylate cement, is injected into the void left by the inflation of balloon 76. A double barrel injection gun nozzle aspirates constantly through the short barrel. Such injection gun nozzle is shown in FIGS. 25 and 26 and includes a material delivery tube 80 and an aspirating tube 82, both of which have open ends 84 and 86, respectively. Injection of synthetic bone material is monitored using lateral fluoroscopy. Leakage posteriorly into the canal of tube 82 requires an abrupt stopping of the injection. Leakage anteriorly is exceedingly rare since the anterior longitudinal ligament is intact with these fractures.

The volume of injection ranges between 3 and 5 cc's. A larger volume is injected than one would predict from the size of the chamber formed with balloon 76 even in those patients injected prophylactically.

Figure 28:
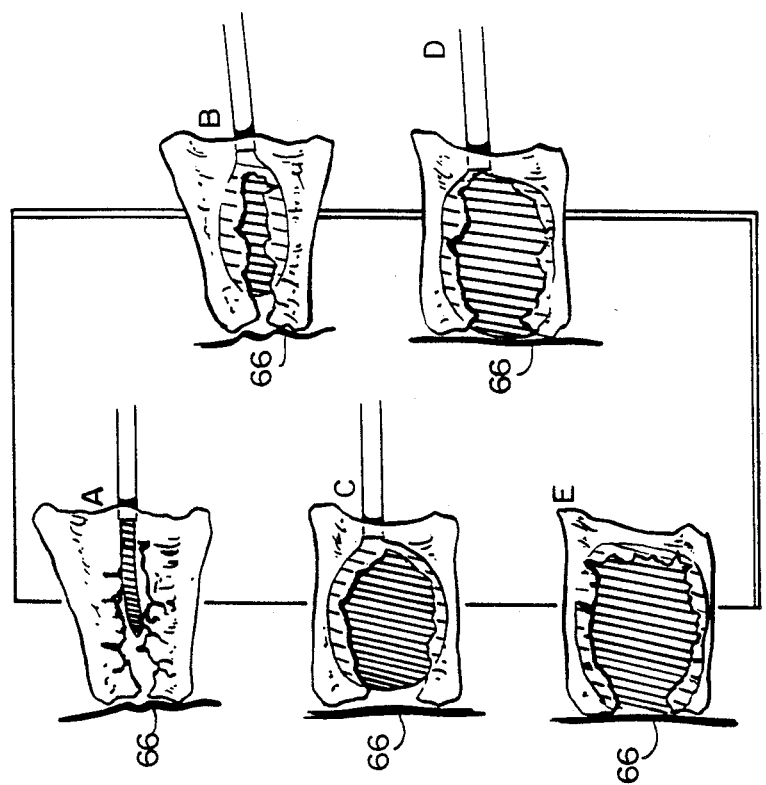
FIG. 28A is a schematic side view of a vertebral body showing the initial insertion of an elliptical inflatable device in the vertebral body and before inflation of the device.
FIG. 28B is a view similar to FIG. 28A but showing partial inflation of the inflatable device of FIG. 28A to initiate a cavity or passage in the bone marrow of the vertebral body.
FIG. 28C is a view similar to FIG. 28B but showing a checker-shaped inflatable device in the vertebral body to further compact the osteoporotic bone marrow in the vertebral body.
FIG. 28D is a view similar to FIG. 28C but showing the initial injection stage in which liquid bone or methyl methacrylate cement is injected into the vertebral body.
FIG. 28E is a view similar to FIG. 28D but showing the vertebral body after the liquid bone or methyl methacrylate cement has set to a hardened condition.
Figure 27:
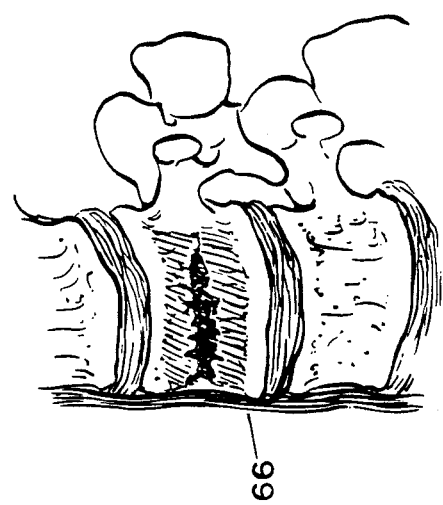
FIG. 27 is a side elevational view of the vertebral body after the liquid bone has been injected into the interior thereof.

The injection gun nozzle shown in FIG. 26 is slowly removed as the vertebral body is injected with artificial bone or cement. At the entry hole into the vertebral body the tip of the injection nozzle is twisted as the cement sets up. At that time, the injection gun nozzle should be removed. FIGS. 28A and 28B show the sequence of the expansion of elliptical balloon 65. FIGS. 28C and 28D show checker-shaped balloon 76 in the vertebral body 66. FIG. 28E shows the vertebral body after the mass 81 of artificial bone or methyl methacrylate cement has set to a hardened condition.

After the proper volume of artificial bone or cement has been inserted into the void of the vertebral body, cannula 30 is removed and the skin is dressed with a bandage.

Surgical protocol for Colles' fractures are described as follows with reference to FIGS. 29–32.

The current treatment for distal radius fractures of the wrist in osteoporotic patients includes: (1) closed reduction and application of a short arm cast with the wrist in a flexed position for six weeks; (2) application of a short arm cast without reduction of the fracture; and (3) closed reductions of the fracture with Chinese finger traps and application of pins and plaster. All three techniques require cast immobilization for 6 to 8 weeks and result in considerable stiffness for many months. In the case of the second treatment described, the wrist is also malpositioned.

The treatment of the present invention involves the reduction of the fracture with Chinese finger traps and the subsequent use of a balloon to create a chamber followed by the injection of either methyl methacrylate cement or a flowable bone substitute into the chamber to fix the fracture. Immobilization would only be a removable splint for two to four weeks. The wrist would be exercised daily to prevent the subsequent stiffness which usually follows wrist fracture.

The steps involved in this procedure are the same as those listed for the percutaneous fixation of vertebral body fractures. The Colles' fracture is positioned this time using finger traps 90 as shown in FIGS. 29 and 30. Local anesthesia is injected. The hand and forearm are prepped in the usually sterile fashion. A smooth guide pin 92 (FIG. 31) is inserted from the tip of the styloid at a 45° angle across the fracture 93. This is followed by a soft tissue expander and then a 2 mm cannula 91. A 2 mm drill 94 (FIG. 32) is then used to drill a canal or passage across the fracture using fluoroscopic control. The drill and guide pin are removed and a gourd-shaped distal radius balloon 95 is introduced into the fracture region through the cannula. The balloon 95 has a configuration substantially the same as that of the inner surface of the cortical bone. The deflated diameter of a globe-shaped part 95a of balloon 95 is in the range of 7 to 10 mm, the overall length L is in the range of 4 to 7 cm, and cylindrical part 95b has a length in the range of 5 to 8 mm.

The balloon 95 is expanded with contrast liquid using x-ray control. Expansion of the balloon 95 causes compacting of the osteoporotic bone marrow against the inner surface of the cortical wall. The balloon is then deflated and the cavity is then injected with a mass 97 of either methyl methacrylate cement or liquid bone substitute. A splint is used for two to four weeks.

Figure 34:
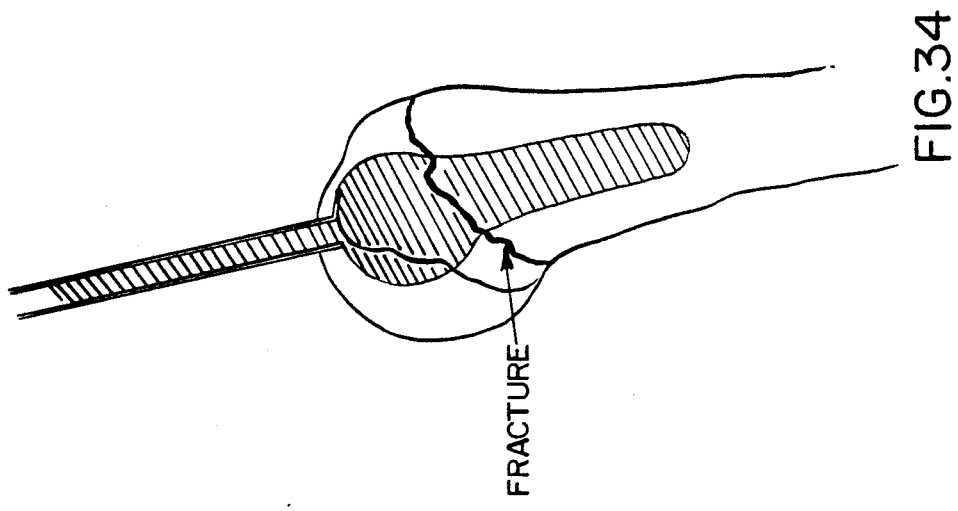
FIG. 34 is a view similar to FIG. 33 but showing the bone fracture and cavity to be filled with liquid bone or methyl methacrylate cement.
Figure 33:
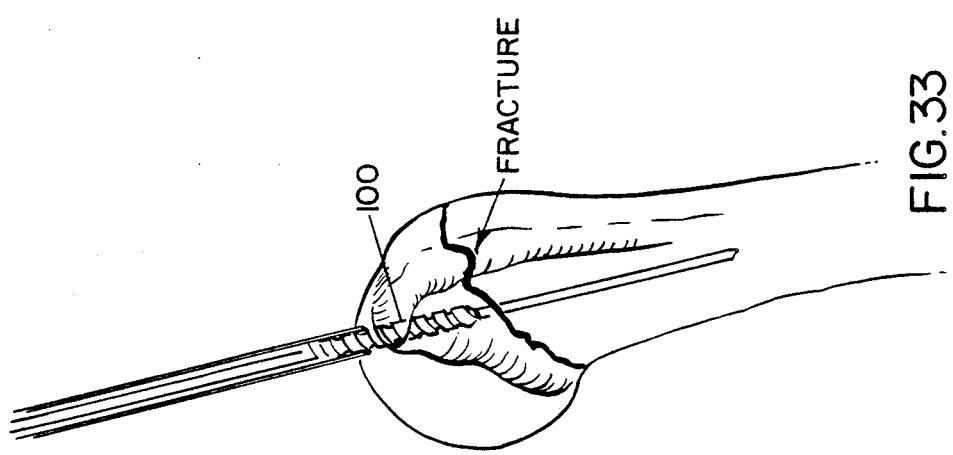
FIG. 33 is a side elevational view of a shoulder showing a fracture therein.

Surgical protocol for the percutaneous fixation of proximal humerus fractures is as follows, with reference to FIGS. 33 and 34:

Percutaneous intra-osseous balloon fixation is indicated for all one-part shoulder fractures (i.e. non-displaced shoulder fractures), all two-part shoulder fractures except greater tuberosity fractures, and all three-part fractures that do not include a prominent elevation of the greater tuberosity or could be better treated with a hemiarthroplasty. It is not now indicated for four-part fractures.

The fracture is reduced with the patient sitting upright. The fracture is injected with local anesthesia as is the area just posterior to the greater tuberosity where a guide pin will be introduced. The fracture is reduced with traction and held by an assistant. A guide pin is introduced through the head of the humerus just posteriorly to the greater tuberosity and followed fluoroscopically across the fracture to approximately 8 cm below the fracture. The soft tissue expander is introduced followed by the 3 mm cannula. A canal is drilled over the guide pin with a 3 mm drill 100 and the drill and guide pin are removed.

A gourd-shaped proximal humerus inflatable device or balloon is introduced into the cavity and inflated using contrast and fluoroscopic control. The balloon is then removed and then the cavity is injected with a mass 101 of either methyl methacrylate cement or a liquid artificial bone substitute as shown in FIG. 34. The fracture is held until the injected substance hardens. The entry site on the top of the shoulder is dressed with a steri-strip and the patient is given a sling for 2 to 4 weeks. During those weeks, the patient should remove the sling several hours a day but perform no heavy lifting.

The gourd-shaped proximal humerus balloon has a configuration substantially the same as that of balloon 95 (FIGS. 31 and 32). The diameter of the globe-shaped part of the proximal humerus balloon is in the range of 14 to 20 mm. The diameter of the cylindrical part is in the range of 6 to 8 mm, and its length is in the range of 8 to 14 cm.

We claim:

1. A method of fixation of a fracture or impending fracture of an osteoporotic bone having osteoporotic bone marrow therein comprising:
   forming a passage in the bone marrow;
   compacting the bone marrow to increase the volume of said passage and
   filling the passage with a flowable material capable of setting to a hardened condition.

2. A method as set forth in claim 1, wherein said compacting step includes forcing the osteoporotic bone marrow outwardly and against the site of the fracture or impending fracture.

3. A method as set forth in claim 1, wherein said compacting step includes forcing the osteoporotic bone marrow outwardly of the central portion of the bone.

4. A method as set forth in claim 3, wherein said forcing step includes direction the osteoporotic bone marrow against an inner surface of the bone within the fracture or impending fracture.

5. A method as set forth in claim 1, wherein said compacting step includes inflating an inflatable device in said passage to urge the osteoporotic bone marrow therein.

6. A method as set forth in claim 5, wherein is included the step of inserting the device in the passage before the inflating step.

7. A method as set forth in claim 1, wherein said forming step includes drilling said osteoporotic bone marrow to form said passage.

8. A method as set forth in claim 7, wherein said drilling step includes guiding a drill through into the proximate corticol bone marrow.

9. A method as set forth in claim 7, wherein said forming step includes drilling the osteoporotic bone marrow to a predetermined depth.

10. A method as set forth in claim 9, wherein said depth is in the range of approximately 60 to 80% of the maximum oblique dimension of the bone containing the osteoporotic bone marrow.

11. A method as set forth in claim 1, wherein the fracture is a fracture of a vertebral body of the human spine.

12. A method as set forth in claim 1, wherein said fracture is a Colles' fracture of the distal radius.

13. A method as set forth in claim 1, wherein said fracture is a fracture of the proximal humerus.

14. A method as set forth in claim 1, wherein said flowable material is selected from the group consisting of liquid synthetic bone and methyl methacrylate cement.

15. A method of fixation of an osteoporotic fracture of a bone containing osteoporotic bone marrow therein comprising:
    drilling said bone to form a passage therein;
    inserting an inflatable device in said recess;
    inflating the device in the passage to increase the volume thereof and to force the osteoporotic bone marrow outwardly of the passage and against the bone to form a void in the bone; and
    filling the void in the bone with a flowable material capable of setting to a hardened condition.

16. A method as set forth in claim 15, wherein said inflating step includes inflating a chambered bladder device having an elliptical configuration.

17. A method as set forth in claim 15, wherein said inflating step includes inflating a chambered bladder device having generally cylindrical configuration.

18. A method as set forth in claim 15, wherein is included the step of guiding a drill into the bone.

19. A method as set forth in claim 15, wherein said inflating step includes inflating the device with a radio-opaque material.

20. A method as set forth in claim 16, wherein said inflating step includes compacting the osteoporotic bone marrow against the bone at the fracture site thereof.

21. A method as set forth in claim 15, wherein said inflating step includes forcing the osteoporotic bone marrow outwardly of the central portion of the bone.

22. A method as set forth in claim 21, wherein said inflating step includes compacting the osteoporotic bone marrow against an inner surface of the bone.

23. A method as set forth in claim 15, wherein said drilling step includes guiding a drill into the bone, and rotating the drill about its longitudinal axis.

24. A method as set forth in claim 23, wherein said drilling step includes drilling the osteoporotic bone marrow to a predetermined depth.

25. A method as set forth in claim 24, wherein said depth is in the range of approximately 60 to 80% of the maximum oblique dimension of the bone.

26. A method as set forth in claim 15, wherein the fracture is a fracture of a vertebral body of the human spine.

27. A method as set forth in claim 15, wherein said fracture is a Colles' fracture of the distal radius.

28. A method as set forth in claim 15, wherein said fracture is a fracture of the proximal humerus.

* * * * *